United States Patent [19]

Ikarashi et al.

[11] Patent Number: 5,194,668
[45] Date of Patent: Mar. 16, 1993

[54] PROCESS FOR PRODUCTION OF CARBOXYLIC ACID ESTERS AND FORMAMIDE

[75] Inventors: Hideo Ikarashi; Hirofumi Higuchi; Koichi Kida, all of Niigata, Japan

[73] Assignee: Mitsubishi Gas Chemical Company, Inc., Tokyo, Japan

[21] Appl. No.: 535,751

[22] Filed: Jun. 8, 1990

[30] Foreign Application Priority Data

Jul. 18, 1989 [JP] Japan .................................. 1-184948

[51] Int. Cl.$^5$ .............................................. C07C 69/76
[52] U.S. Cl. ...................... 560/103; 560/38; 560/60; 560/106; 560/155; 560/173; 560/179; 560/188; 560/205; 560/215; 560/265; 564/137
[58] Field of Search ............... 560/103, 38, 60, 155, 560/179, 215, 265, 106, 173, 188, 208

[56] References Cited

U.S. PATENT DOCUMENTS 4,613,684  9/1986  Aoyama et al. ................. 510/179
4,973,739 11/1990  Nagasawa et al. ............... 560/103

FOREIGN PATENT DOCUMENTS 0342475 11/1989  European Pat. Off. .
  23209  5/1962  Fed. Rep. of Germany .
58-55444  4/1983  Japan .

OTHER PUBLICATIONS

Chemische Berichte vol. 87, 1954, pp. 537–546, H. Bredereck et al.: "Umsetzungen von Halogenverbindungen mit Formamid".
Patent Abstracts of Japan, vol. 3, No. 83 (C-52), Jul. 1979, JP-A-5459234, "Preparation of Aromatic Dicarbamide".

Primary Examiner—Paul J. Killos
Attorney, Agent, or Firm—Frishauf, Holtz, Goodman & Woodward

[57] ABSTRACT

Carboxylic acid esters and formamide are efficiently obtained by reacting carboxylic acid amides and formic acid esters, or by reacting carboxylic acid amides, alcohols and carbon monoxide in the presence of a dehydrated condensate of carboxylic acid amide with an alkali metal hydroxide or an alkaline earth metal hydroxide catalyst.

24 Claims, No Drawings

PROCESS FOR PRODUCTION OF CARBOXYLIC ACID ESTERS AND FORMAMIDE

BACKGROUND OF THE INVENTION

1. Field of the Invention

The present invention relates to a process for efficient production of carboxylic acid esters and formamide by reacting carboxylic acid amides and formic acid esters, or by reacting arboxylic acid amides, alcohols, and carbon monoxide.

2. Description of the Related Arts

Carboxylic acid esters are industrially important compounds. As methods of producing carboxylic acid esters from carboxylic acid amides, (1) a method of producing methyl acetate from acetic acid amide, (2) a method of producing methyl methacrylate from methacrylic acid amide, (3) a method of producing methyl acrylate from acrylic acid amide, and (4) a method of producing methyl α-hydroxyisobutyrate from α-hydroxyisobutyric acid amide are known.

Formamide is used as a solvent, a treating agent, an electrolyte, or an antifreezing agent, or as an intermediate for production of dyes, pigments, medicines and so on. Moreover formamide is an important basic chemical compound which can be used also as a starting material for production of hydrogen cyanide.

For production of carboxylic acid esters from carboxylic acid amides, a method of reacting carboxylic acid amides and alcohols in the presence of sulfuric acid has heretofore been known, and this method is widely employed for industrial production of methyl methacrylate.

The above method, however, has disadvantages in that a large amount of acidic ammonium sulfate results as a byproduct, leading to a marked increase in production costs owing to its disposal, and an expensive corrosion-resistant apparatus is also required.

In order to overcome the above problems, a method of producing carboxylic acid esters by catalytic reaction of carboxylic acid amides and alcohols without sulfuric acid has been proposed.

This method, however, has disadvantages in that yield and selectivity of the desired carboxylic acid ester are low, a large amount of ammonia is formed and requires separation and recovery, and an ammonium salt of carboxylic acid is also formed. Thus the method is not satisfactory in commercial practice.

As a method not accompanied by formation of ammonia, Japanese Patent Application Laid-Open Nos. 55444/1983 and 78937/1985 disclose a method of producing carboxylic acid ester and formamide by reacting carboxylic acid amide and formic acid ester in the presence of a catalyst comprising an organic or inorganic acid metal salt, or a metal carbonyl compound, and a nitrogen or phosphorus-containing organic compound.

These methods, however, have problems that the catalyst system is complicated and expensive, and catalyst recovery costs are high.

SUMMARY OF THE INVENTION

An object of the present invention is to provide a process for producing carboxylic acid esters and formamide from carboxylic acid amides and formic acid esters with high efficiency under mild conditions.

Another object of the present invention is to provide a highly efficient process for producing carboxylic acid esters and formamide at a low production cost using an inexpensive apparatus instead of an expensive corrosion-resistant apparatus.

The present invention provides a process for production of carboxylic acid esters and formamide by reacting carboxylic acid amides and formic acid esters or by reacting carboxylic acid amide, alcohols and carbon monoxide in the presence of dehydrated condensates of carboxylic acid amide with alkali metal hydroxide or with alkaline earth metal hydroxide.

DESCRIPTION OF PREFERRED EMBODIMENTS

Carboxylic acid amides to be used in the present invention include aliphatic or aromatic carboxylic acid amides, α-hydroxycarboxylic acid, and α-aminocarboxylic acid amides. These amides can be prepared by subjecting nitriles to hydration, or by reacting amines and carbon monoxide. Specific examples are acetamide, lactic acid amide, acrylic acid amide, methacrylic acid amide, α-hydroxyisobutyric acid amide, benzamide, and alanineamide.

Alcohols to be used in the present invention are preferably aliphatic alcohols having 1 to 10 carbon atoms. Formic acid esters are preferably esters of the above alcohols and formic acid. Specific examples of the aliphatic alcohols are methanol, ethanol, 1-propanol, 2-propanol, 1-butanol, 2-butanol, and 1-pentanol. Specific examples of formic acid esters are methyl formate, ethyl formate, propyl formate, isopropyl formate, n-butyl formate, sec-butyl formate, and n-pentyl formate.

Dehydrated condensates of carboxylic acid amide and alkali metal hydroxide or alkaline earth metal hydroxide to be used in the process of the present invention can be easily prepared by mixing carboxylic acid amide with alkali metal hydroxide or with alkaline earth metal hydroxide and then heating the resulting mixture to remove water therefrom.

Alkali metal hydroxide include hydroxides of lithium, sodium, potassium, rubidium or cesium, and sodium hydroxide is economically preferable.

Alkaline earth metal hydroxides include hydroxides of magnesium, calcium, strontium or barium.

In the process of the present invention, when formic acid ester and carboxylic acid amide are used as the starting materials, it is desirable to use a suitable solvent, because carboxylic acid amide is generally in a solid state at room temperature.

As the solvent, a polar solvent, e.g., alcohols, is preferably used. It is particularly preferred to use an alcohol corresponding to the formic acid ester.

When alcohol and carbon monoxide are used in place of formic acid ester as the starting materials, it is preferred that the alcohol is used in an excess amount so that it can also function as a solvent for carboxylic acid amide.

In the reaction of carboxylic acid amide and formic acid ester in the process of the present invention, the amount of the formic acid ester used is 0.5 to 20 mol, preferably 1.5 to 8 mol per mol of the carboxylic acid amide.

If the amount of formic acid ester is under the range, the conversion of carboxylic acid amide becomes low. On the other hand, if the amount is above the range, the amount of unreacted formic acid ester undesirably increases, which is not suitable for practical use.

In the reaction of carboxylic acid amide, alcohol and carbon monoxide in the process of the present invention, the amount of the alcohol used is 1 to 30 mol, preferably 3 to 20 mol per mol of the carboxylic acid amide.

If the amount of alcohol is under the range, carboxylic acid amide can not be dissolved. On the other hand, if the amount is above the range, the recovered amount of alcohol from reaction solution undesirably increases, which is not suitable for practical use.

In the present invention, carboxylic acid amide can be reacted with formic acid ester, alcohol and carbon monoxide. In this case, the amounts of formic acid ester and alcohol used are 0.5 to 15 mol and 0.5 to 30 mol, preferably 1 to 8 mol and 2 to 15 mol, respectively, per mol of carboxylic acid amide.

Dehydrated condensates of carboxylic acid amide with alkali metal hydroxide or with alkaline earth metal hydroxide can be usually prepared by using carboxylic acid amide in an excess amount. That is, said dehydrated condensate can be produced by mixing alkali metal hydroxide or alkaline earth metal hydroxide with carboxylic acid amide in the range of 0.001 to 0.8 mol, preferably 0.005 to 0.5 mol of the hydroxide, per mol of the carboxylic acid amide, and heating the resulting mixture, and then dehydrating under atmospheric pressure or under reduced pressure, at a temperature of 50° to 200° C., preferably 80° to 150° C.

It is desirable to remove the generated water rapidly from the reaction system by using inert gas such as nitrogen or using azeotropic solvent such as toluene.

In the reaction of carboxylic acid amide with formic acid ester, the amounts of alkali metal hydroxides or alkaline earth metal hydroxides are usually 0.001 to 0.3 mol, preferably 0.003 to 0.1 mol, per mol of carboxylic acid amide. That is, if the above range is satisfied, dehydrated condensates prepared in the reaction system where carboxylic acid amide is excessive, may be used as they are. Or said dehydrated condensates may be used after adjusting to the desired proportion of the amount by adding carboxylic acid amide again.

Carboxylic acid amide in the present invention may be used singly or in a mixture of two kinds or more. Further, carboxylic acid amides for preparation of dehydrated condensates may be identical to or different form carboxylic acid amide for reaction with formic acid ester.

The reaction temperature and period of time can be chosen from a wide range depending on the kind of the starting material, the amount of the catalyst charged, and the desired conversion. In general, the reaction temperature is preferably 0° to 200° C. and more preferably 20° to 150° C. If the reaction temperature is less than 0° C., a rate of reaction is too low for practical use, and if it is more than 200° C., decomposition of formamide and deactivation of the catalyst undesirably occur. The reaction period of time is preferably 0.1 to 20 hours and more preferably 0.2 to 10 hours.

In connection with the pressure in the reaction of carboxylic acid amide and formic acid ester in the present invention, although the reaction may be carried out under a vapor pressure at the reaction temperature, it can also be carried out under a pressure of carbon monoxide in order to prevent decomposition of formic acid ester. Specifically, the reaction pressure should be between atmospheric pressure and 300 atm, and from an economic standpoint, it is preferably between atmospheric pressure and 100 atm.

In the reaction of carboxylic acid amide, alcohol and carbon monoxide, the reaction pressure is in a range of 10 to 500 atm, preferably 30 to 200 atm as a partial pressure of carbon monoxide.

The process of the present invention can be carried out batchwise or continuously. Industrially a continuous process is preferred.

In accordance with the process of the present invention, carboxylic acid esters and formamide can be produced with high selectivity under mild reaction conditions from carboxylic acid amides and formic acid esters by the use of dehydrated condensates of carboxylic acid amide with alkali metal hydroxide or with alkaline earth metal hydroxide as a catalyst. Thus the process of the present invention is of great significance from an industrial standpoint, since the catalysts used are inexpensive.

The present invention is described in greater detail with reference to the following examples, although it is not intended to be limited thereto.

EXAMPLE 1

Into a 100 milliliter 3-necked flask with a stirrer, 10.3 g (0.1 mol) of α-hydroxyisobutyric acid amide was placed, and 0.12 g (0.003 mol) of powdery sodium hydroxide was added thereto, and the mixture was stirred and heated at 50 torr at 120° C. for 0.5 hour, to distill away resulting water.

Then, the pressure was returned to the atmospheric pressure, and a reflux-condenser was attached to the flask. After 9.6 g of methanol was added dropwise while cooling gradually, said solution was cooled to room temperature.

The solution was transferred into a 120-ml stainless steel autoclave, and 12.6 g (0.21 mol) of methyl formate was added, and the mixture was reacted at 60° C. for 2 hours.

The autoclave was cooled to 10° C., and then the product was taken out thereof and was subjected to a gas chromatographic analysis.

As the result, the conversion of α-hydroxyisobutyric acid amide was 63.4%, and the selectivity into methyl α-hydroxyisobutyrate was 99.1%.

The selectivity into formamide (based on the reacted α-hydroxyisobutyric acid amide) was 99.5%.

EXAMPLE 2

Into a 500 ml 3-necked flask equipped with a stirrer and a reflux-condenser with a distilling receiver, 51.5 g (0.5 mol) of α-hydroxyisobutyric acid amide and 150 ml of toluene were placed, 2.03 g (0.051 mol) of powdery sodium hydroxide was added thereto and the mixture was heated and stirred for 1.5 hours to reflux toluene, and about 1 ml of resulting water was obtained.

Then, the flask was cooled to room temperature, and after toluene was removed by decantation, 80 g of methanol was added and heated at 50° C., to obtain 133 g of methanol solution.

Said solution was transferred into a 500 ml stainless steel autoclave, and 132.2 g (2.2 mol) of methyl formate was added, and then the mixture was reacted at 70° C. for 2 hours.

The autoclave was cooled to 10° C., and then the product was taken out and was subjected to a gas chromatographic analysis.

As the result, the conversion of α-hydroxyisobutyric acid amide was 80.2%, and the selectivity into methyl α-hydroxyisobutyrate was 98.8%. The selectivity into formamide was 99.0%.

COMPARATIVE EXAMPLE 1

Into 120 ml stainless steel autoclave, 10.3 g (0.1 mol) of α-hydroxyisobutyric acid amide, 0.12 g (0.003 mol) of powdery sodium hydroxide, 9.6 g of methanol and 12.6 g (0.21 mol) of methyl formate were placed, and the mixture was heated and stirred at 60° C. for 2 hours.

The autoclave was cooled to 10° C., and then the content was taken out and was subjected to a gas chromatographic analysis.

As the result, the yield of methyl α-hydroxyisobutyrate (based on the α-hydroxyisobutyric acid amide) was 2.1%, and the yield of formamide was 2.5%.

EXAMPLE 3

The same procedure of Example 1 was repeated with the exception that 5.9 g (0.1 mol) of acetamide was used as the carboxylic acid amide.

The conversion of acetamide was 69.1%, and the selectivity into methyl acetate was 97.4%. The selectivity into formamide was 98.0%.

EXAMPLE 4

The same procedure of Example 1 was repeated with the exception that 8.5 g (0.1 mol) of methacrylic acid amide was used as the carboxylic acid amide and the resulting water was distilled away at 30 torr for 10 minutes.

The conversion of methacrylic acid amide was 84.8%, and the selectivity into methyl methacrylate was 83.4%. The selectivity into formamide was 92.2%.

EXAMPLE 5

The same procedure of Example 1 was repeated with the exception that 12.2 g (0.1 mol) of nicotinic acid amide was used as the carboxylic acid amide.

The conversion of nicotinic acid amide was 71.8%, and the selectivity into methyl nicotinate was 96.6%. The selectivity into formamide was 97.6%.

EXAMPLE 6

In the same 3-necked flask as used in Example 1, 0.9 g (0.02 mol) of formamide was placed. 0.12 g (0.003 mol) of powdery sodium hydroxide was added thereto and the mixture was heated and stirred at 100 torr at 60° C. for 0.5 hour. Then, the resulting water was distilled away to prepare formamide solution of dehydrated condensate.

Said solution was transferred into the same autoclave as used in Example 1, 12.8 g (0.4 mol) of methanol, 10.3 g (0.1 mol) of α-hydroxyisobutyric acid amide and 18.0 g (0.3 mol) of methyl formate were added thereto, and the mixture was reacted at 60° C. for 2 hours.

The conversion of α-hydroxyisobutyric acid amide was 70.6% and the selectivity into methyl α-hydroxyisobutyrate was 98.1%. The selectivity into formamide was 96.0%.

EXAMPLE 7

The same procedure was carried out as in Example 1 with the exception that 51 g (0.5 mol) of butyl formate was used in place of methyl formate and 22.2 g (0.3 mol) of butanol was used in place of methanol.

The conversion of α-hydroxyisobutyric acid amide was 67.4% and the selectivity into butyl α-hydroxyisobutyrate was 95.5%. The selectivity into formamide was 97.4%.

EXAMPLE 8

The same procedure was carried out as in Example 1 with the exception that 0.28 g (0.005 mol) of potassium hydroxide was used in place of sodium hydroxide.

The conversion of α-hydroxyisobutyric acid amide was 64.6% and the selectivity into methyl α-hydroxyisobutyrate was 98.6%. The selectivity into formamide was 99.5%.

EXAMPLE 9

The same procedure was carried out as in Example 1 with the exception that 1.71 g (0.01 mol) of barium hydroxide was used in place of sodium hydroxide.

The conversion of α-hydroxyisobutyric acid amide was 52.8% and the selectivity into methyl α-hydroxyisobutyrate was 96.1%. The selectivity into formamide was 98.4%.

EXAMPLE 10

In the same 3-necked flask as used in Example 1, 5.2 g (0.05 mol) of α-hydroxyisobutyric acid amide was placed and 0.08 g (0.002 mol) of powdery sodium hydroxide was added thereto, and the mixture was heated and stirred at 120° C. for 1.5 hours, to distill away the resulting water.

Then, the mixture containing substantially no water was cooled to room temperature and dissolved with 11.4 g of methanol.

Said solution was transferred into the same autoclave as used in Example 1, subjected to pressure of carbon monoxide, and then heated and stirred.

When the temperature in the autoclave reached at 80° C., the reaction was continued for 3 hours while introducing carbon monoxide to maintain the reaction pressure at 40 atm.

Then, the autoclave was cooled to 10° C. After the internal pressure was gradually reduced to atmospheric pressure, the product was taken out and subjected to analysis.

As the result, the conversion of α-hydroxyisobutyric acid amide was 83.9% and the selectivity into methyl α-hydroxyisobutyrate was 99.4%. The selectivity into formamide was 93.5%

What is claimed is:

1. A process for the production of carboxylic acid ester and formamide which comprises reacting carboxylic acid amide and formic acid ester at a pressure of atmospheric pressure to 300 atmospheres, at a temperature of 0° to 150° C. and for a period of time of 0.1 to 20 hours in the presence of (a) dehydrated condensates of carboxylic acid amide and (b) an alkali metal hydroxide or an alkaline earth metal hydroxide, said formic acid ester being in an amount of 0.5 to 20 mol per mol of the carboxylic acid amide.

2. A process for the production of carboxylic acid ester and formamide which comprises reacting carboxylic acid amide, alcohol and carbon monoxide at a temperature of 0° to 150° C. for a period of time of 0.1 to 20 hours in the presence of (a) dehydrated condensates of carboxylic acid amide and an alkali metal hydroxide or (b) an alkaline earth metal hydroxide, said alcohol being in an amount of 1 to 30 mol per mol of the carboxylic acid amide.

3. The process as claimed in claim 1 or 2, wherein the alkali metal hydroxide is at least one selected from the group consisting of lithium hydroxide, sodium hydroxide, potassium hydroxide, rubidium hydroxide and cesium hydroxide.

4. The process as claimed in claim 1 or 2 wherein the alkaline earth metal hydroxide is at least one selected from the group consisting of magnesium hydroxide, calcium hydroxide, strontium hydroxide and barium hydroxide.

5. The process as claimed in claim 1 or 2 wherein the carboxylic acid amide as starting material is aliphatic carboxylic acid amide, aromatic carboxylic acid amide, α-hydroxycarboxylic acid amide, or α-aminocarboxylic acid amide.

6. The process as claimed in claim 1 or 2 wherein the carboxylic acid amide as a starting material is at least one compound selected from the group consisting of acetamide, lactic acid amide, acrylic acid amide, methacrylic acid amide, benzamide, α-hydroxyisobutyric acid amide, nicotinic acid amide and alanineamide.

7. The process as claimed in claim 1, wherein the formic acid ester is at least one compound selected from the group consisting of methyl formate, ethyl formate, propyl formate, isopropyl formate, n-butyl formate, sec-butyl formate, and n-pentyl formate.

8. The process as claimed in claim 1, wherein the formic acid ester is methyl formate.

9. The process as claimed in claim 2, wherein the alcohol is an aliphatic alcohol having 1 to 10 carbon atoms.

10. The process as claimed in claim 2, wherein the alcohol is at least one compound selected from the group consisting of methanol, ethanol, 1-propanol, 2-propanol, 1-butanol, 2-butanol, and 1-pentanol.

11. The process as claimed in claim 2, wherein the alcohol is methanol.

12. The process as claimed in claim 1 or 2 wherein the carboxylic acid amide constituting the dehydrated condensates is identical to carboxylic acid amide as a starting material.

13. The process as claimed in claim 1 or 2 wherein the carboxylic acid amide constituting the dehydrated condensates is different from carboxylic acid amid as a starting material.

14. The process as claimed in claim 1, wherein said formic acid ester is in an amount of 1.5 to 8 mol per mol of the carboxylic acid amide.

15. The process as claimed in claim 1, wherein the temperature is 20° to 150° C., the period of time is 0.2 to 10 hours and the pressure is atmospheric pressure to 100 atmospheres.

16. The process as claimed in claim 2, wherein said alcohol is in an amount of 3 to 20 mol per mol of the carboxylic acid amide.

17. The process as claimed in claim 16, wherein the process is conducted at a pressure of 10 to 500 atmospheres, measured as a partial pressure of carbon monoxide.

18. The process as claimed in claim 17, wherein the pressure is 30 to 200 atmospheres, the temperature is 20° to 150° C. and the period of time is 0.2 to 10 hours.

19. The process as claimed in claim 1, wherein the dehydrated condensate of carboxylic acid amide with an alkali metal hydroxide or with an alkaline earth metal hydroxide is prepared by mixing 0.001 to 0.8 mol of an alkali metal hydroxide or an alkaline earth hydroxide per mol of carboxylic acid amide, heating the resulting mixture under atmospheric or reduced pressure and then conducting dehydration at a temperature of 50° to 200° C.

20. The process as claimed in claim 2, wherein the dehydrated condensate of carboxylic acid amide with an alkali metal hydroxide or with an alkaline earth metal hydroxide is prepared by mixing 0.001 to 0.8 mol of an alkali metal hydroxide or an alkaline earth hydroxide per mol of carboxylic acid amide, heating the resulting mixture under atmospheric or reduced pressure and then conducting dehydration at a temperature of 50° to 200° C.

21. The process as claimed in claim 14, wherein the carboxylic acid amide as a starting material is at least one compound selected from the group consisting of acetamide, lactic acid amide, acrylic acid amide, methacrylic acid amide, benzamide, α-hydroxyisobutyric acid amide, and alanineamide and the formic acid ester is at least one compound selected from the group consisting of methyl formate, ethyl formate, propyl formate, isopropyl formate, n-butyl formate, sec-butyl formate and n-pentyl formate.

22. The process as claimed in claim 17, wherein the carboxylic acid amide as a starting material is at least one compound selected from the group consisting of acetamide, lactic acid amide, acrylic acid amide, methacrylic acid amide, benzamide, α-hydroxyisobutyric acid amide, alanineamide and nicotinic acid amide, and the alcohol is at least one compound selected from the group consisting of methanol, ethanol, 1-propanol, 2-propanol, 1-butanol, 2-butanol and 1-pentanol.

23. The process as claimed in claim 1, wherein the carboxylic acid amide is α-hydroxyisobutyric acid amide and the formic acid ester is methyl formate.

24. The process as claimed in claim 1, wherein the carboxylic acid amide is α-hydroxyisobutyric acid amide and the formic acid amide is butyl formate.

* * * * *